United States Patent [19]

Boggs et al.

[11] 4,325,417

[45] Apr. 20, 1982

[54] CONNECTOR MEMBER FOR SEALED CONDUITS UTILIZING CRYSTALLINE PLASTIC BARRIER MEMBRANE

[75] Inventors: Daniel R. Boggs, Vernon Hills; Peter C. Kwong, Palatine; Dean G. Laurin, Lake Zurich, all of Ill.

[73] Assignee: Baxter Travenol Laboratories, Inc., Deerfield, Ill.

[21] Appl. No.: 27,575

[22] Filed: Apr. 6, 1979

[51] Int. Cl.$^3$ .............................................. B65B 3/04
[52] U.S. Cl. ..................................... 141/98; 141/383; 219/221; 222/541; 250/338; 285/3; 285/67
[58] Field of Search ..................... 141/1, 98, 392, 114, 141/311 R; 156/272, 289, 250, 251, 252, 253, 261, 306; 222/541; 285/3, 4, 67, 325; 250/338; 219/221

[56] References Cited

U.S. PATENT DOCUMENTS 4,022,256 5/1977 Berkman et al. .................. 141/1

*Primary Examiner*—Houston S. Bell, Jr.
*Attorney, Agent, or Firm*—Paul C. Flattery; John A. Caruso; Garrettson Ellis

[57] ABSTRACT

A connector member for a fluid flow path is provided which comprises a transparent housing enclosing an opaque barrier membrane or wall portion blocking flow through the flow path. The barrier membrane is adapted to be openable by exposure to radiant energy from the exterior through the transparent housing. In accordance with this invention, the barrier membrane is made of a predominantly crystalline plastic material, and, accordingly, exhibits a relatively sharp melting point for improved opening characteristics upon exposure to the radiant energy.

22 Claims, 4 Drawing Figures

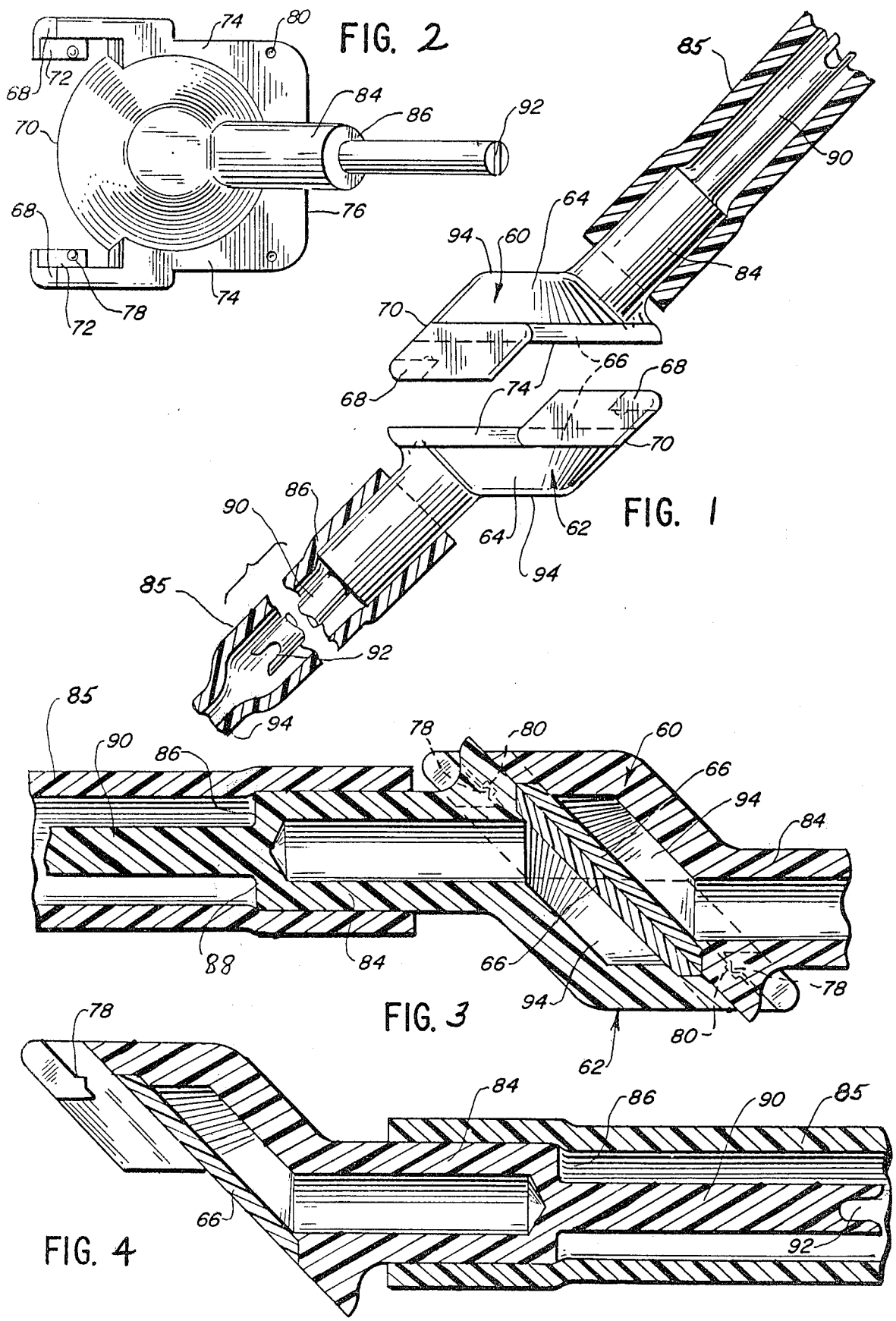

CONNECTOR MEMBER FOR SEALED CONDUITS UTILIZING CRYSTALLINE PLASTIC BARRIER MEMBRANE

BACKGROUND OF THE INVENTION

In U.S. Pat. No. 4,157,723, issued June 12, 1979 and U.S. application No. 005,749 filed Jan. 23, 1979 a novel concept for a sterile connector member is disclosed. The need for sterile connection arises in various fields, for example, in the area of blood banking. At the present time, when a unit of stored blood is taken from the blood bank and partially used, it is not possible to return the remaining portion of the blood back to storage, since the conventional connections which are made, although highly aseptic, constitute at least a technical breach of sterility. Accordingly, the blood cannot be reliably stored any longer without the danger of the growth of bacteria.

Numerous designs for means for accomplishing sterile connection have been proposed, including the idea of obtaining a connection to stored blood for withdrawing of part of the unit in such a manner that the remainder of the unit can be returned to storage for the remainder of its useful life.

The disclosures of the above cited patent applications represent potentially highly effective and successful means for sterile connection, in that opaque barrier membrane means within a sealed transparent housing is exposed to radiant energy to cause the barrier membrane means to fuse or melt, forming a hole in the membrane which establishes the connection. At the same time, if the barrier membrane is a high melting material, the sterility of the connection is assured, since the achievement of the melting point of the barrier membrane can assure the destruction of all bacteria present on the portions of the membrane that are non-sterile.

Particularly, a pair of housings, each carrying an opaque membrane, are brought together with the non-sterile faces of the opaque barrier membrane or walls being brought together into facing relationship. Then, when the opaque walls are exposed to radiant energy, they fuse together, preferably destroying the bacteria by the high melting point of the material, and also entrapping them by the melting process, since the non-sterile faces of the two membranes fuse together.

DESCRIPTION OF THE INVENTION

In this invention, the melting and hole opening characteristics of the barrier membrane or opaque wall of this invention are improved to provide more precision and reliability in the behavior of the connector members of this invention when the opaque barrier membrane is exposed to radiant energy.

Specifically, this invention relates to a connector member for a fluid flow path which comprises a transparent housing enclosing an opaque barrier membrane means or wall, blocking flow through the flow path. The barrier membrane means is adapted to be openable by exposure to radiant energy from the exterior through the transparent housing.

By the improvement of this invention, the barrier membrane means is made of a significantly crystalline plastic material rather than generally amorphous materials as in the prior art, with the result that the barrier membranes melt or soften at a more precise temperature range due to a change of phase and loss of crystallinity through heating, with the result that more effective results in terms of proper and reliable hole opening upon irradiation are exhibited when barrier membranes are fabricated in accordance with this invention in connector members.

It is contemplated that the connector member in accordance with this invention may be fabricated out of a simple unitary, transparent housing having a single opaque barrier membrane which may be disrupted by exposure to radiant energy when an opening through the connector is desired. Such a connector may be part of a fluid flow path in a biological container or the like, providing reliable opening characteristics without exposure of the membrane to the exterior.

The specific embodiment, however, as shown herein includes a pair of transparent housings, each of which carries the opaque barrier membrane or wall of this invention, with the housings being adapted for connection to each other with the opaque wall portions brought together in facing relationship. In this instance, upon exposure to radiant energy, the pair of facing, opaque wall portions can fuse together as a hole opens between them.

Specifically, plastic materials which are significantly crystalline are those which exhibit at least 25 percent and preferably 35 to 70 percent or more crystallinity, as measured by X-ray diffraction in accordance with the teachings of W. O. Stratton in "The Use of X-Ray Diffraction and Scattering in Characterisation of Polymer Structure", *Int. Symp. Plast. Test. Stand.*, Special Technical Publication No. 247, American Society for Testing and Materials, Philadelphia (1959). In the event of the technical difficulty in determining the amount of crystallinity of a specific plastic material by X-ray diffraction, the percentage crystallinity may be determined by a calorimetric technique as described in the article by J. D. Hoffman, J. Am. Chem. Soc. 74 1696–1700 (1952).

The barrier membrane material preferably has a crystalline melting point of at least about 200° C., to provide sterilization as it is opened by melting.

Specifically, examples of materials which are suitable for use in this invention include (a) poly(4-methyl-1-pentene) which is sold under the name TPX by Mitsui Chemical Company (typical crystalline melting point: 235° C.); (b) poly(butylene terephthalate) available from various suppliers (typical crystalline melting point: 221°–232° C.); and (c) various nylon polyamide materials having a desired melting point, including NYLON 11 sold by Rilsan Chemical Company (typical crystalline melting point: 194° C.).

Other significantly crystalline materials which may be used for the opaque wall of this invention include: polyesters such as poly(ethylene terephthalate), having a typical crystalline melting point of 250° C.; or DuPont Hytrel, a block copolymer of polybutylene ether and polybutylene terephthalate having a typical crystalline melting point of 200°–220° C., depending upon the type; polyamide materials such as Nylon 6, having a typical crystalline melting point of 216° C.; Nylon 6—6, having a typical crystalline melting point of 265° C.; Nylon 6-10, having a typical crystalline melting point of 227° C.; and fluorinated hydrocarbon materials such as perfluoroalkoxy polymers, having a typical crystalline melting point of 310° C.; polychlorotrifluoroethylene, having a typical crystalline melting point of 220° C.; and fluorinated ethylene propylene materials having a typical crystalline melting point of 275° C..

Referring to the drawings,

FIG. 1 is an elevational view, taken partly in section, of a pair of connection elements which may be combined together to make a connector member, prior to being so joined together.

FIG. 2 is a top plan view of the connector element of FIG. 1.

FIG. 3 is a fragmentary, vertical sectional view of the connector member made from the joined connector elements of FIG. 1.

FIG. 4 is a longitudinal sectional view of a single connector member of FIG. 3.

Referring to the drawings, the design of connector elements and the connector member which can be made from them shown herein is identical to one embodiment shown in the copending U.S. application Ser. No. 005,749 filed Jan. 23, 1979, except for the change of material of the respective opaque wall portions which results in improved reliability in the design shown. Also, the same improvement and reliability can be obtained in many different designs of connector in accordance with this invention.

The specific embodiment shown herein is intended to be merely exemplary of many embodiments which may utilize the opaque walls made in accordance with this invention.

The drawings show the pair of connector elements 60, 62, each of which comprise the hollow transparent housing 64 and opaque wall 66 sealed at its periphery to the transparent housing 64 in a manner which is similar to the previous embodiments of the cited copending patent applications.

Opaque wall portion 66 is a significantly crystalline thermoplastic material as described which generally contains a filler such as powdered charcoal, activated charcoal, or carbon black to render it opaque, although other desired filters which are absorbent of the type of radiant energy to be used may be provided as a substitute for carbon. The remainder of the housings 64 are shown as being made of a transparent, high melting plastic material such as Lexan polycarbonate, sold by the General Electric Company, or another preferably high melting, transparent, thermoplastic material.

Radiant energy can be provided to the system by means of visible or incandescent, infrared, ultraviolet, or radio-frequency energy as may be desired. The term "opaque" implies that the opaque wall portions are adapted to absorb a relatively high percentage of the particular radiant energy in which it is exposed. The term "transparent" implies that a lower percentage of the radiant energy applied is absorbed. Focused, infrared radiant energy is particularly desirable for use. Lasers may also be used as desired to provide the radiant energy.

The opaque wall portions 66 may be pre-stressed by uniaxial or biaxial orientation, or with radial stress patterns, to facilitate the formation of a central aperture as the opaque wall portions seal together. Also, unstressed wall portions may be used, with the central aperture formation taking place by cohesion during the heat-softening irradiation step.

Retention means are carried by each connector element for retaining the housings 64 together. The retention means include opposed gripper arms 68 adjacent first end 70 of the housing which define a track 72 for receiving a flange 74 of the container element to which connection is to be made.

Opposed flange members 74 are positioned adjacent a second end 76 of each housing 64, the flanges 74 being adapted to fit in sliding, retaining relation with a track 72 defined by the gripper arm means of another connector element, for locking of the two connector elements together, with the opaque walls 66 in facing, abutting relationship as shown in FIG. 3. Opaque walls 66 are fabricated of one or more materials as described above, and may preferably range from 0.002 to 0.06 inch thick, specifically about 0.01 inch, so that the combined initial thickness of the pair of abutting opaque walls is twice that thickness.

Detent means 78, 80 are provided so that the respective connector elements 60, 62 after sliding into connection, abutting relationship are pulled apart again only with substantial difficulty in the common mode of use, where, to insure sterility, the connector elements are intended to be permanently retained together after connection during their period of use. Each connector element 60, 62 defines an integral conduit member 84, the axis of which, in this embodiment, defines an acute angle with the plane of its associated opaque wall portion 66.

As shown herein, the outer end of the conduit member 84 defines a closed end wall 86 defining a thinned, frangible area 88 which may be annular in shape. A projecting member 90 extends outwardly from the closed end wall, so that manual bending of the projecting member 90 can cause rupture of the end wall to permit the opening of the outer end of conduit member 84.

Each conduit member 84 may be positioned in sealed relation within the bore of flexible tubing 85, which may communicate with a sealed container such as a blood bag. Accordingly, manual manipulation of the flexible tubing 85 and projecting member 90 permits the rupturing of end 86 of each conduit member 84 to open the connector elements 60, 62 after they have been connected together into a connector member as shown in FIG. 3.

When both of the connector elements carry the frangibly sealed ends 86 of their conduit member, it is often desirable to open one of them prior to the irradiation step. Then, air which is in the remaining sealed chamber 94 within housing 64 and conduit member 84 will expand during the heating step, providing a pressure differential across opaque walls 66 during the irradiation step. This in turn will assist in the rupturing of the opaque walls 66 as the walls weaken and melt, to provide a preferably sterile, sealed connection between the two connector elements 60, 62.

If desired, only one of the connector elements need to carry sealed end wall 86 and elongated member 90. For example, an empty blood bag might not utilize the sealed end wall 86 and elongated member 90, while a blood bag intended for receiving blood from a donor might carry the sealed end wall, to prevent traces of blood from passing upwardly to the opaque wall 66 during storage.

Elongated member 90 may terminate in a diametric slot 92. After breaking away, the slotted end of elongated member 92 may be pressed into constricted portion 98 of tubing 36i a, to hold member 92 away from broken and open end 86. This prevents occluding of the flow passage. In this instance slot 92 permits flow through constricted portion 94 while member 92 is held therein.

After assembly, the connector element may be irradiated by focused infrared radiation or the like for the desired period of time, sufficient to fuse the opaque wall members 66 to cause the formation of a hole through the wall members for achievement of sterile connection. Improved hole opening is achieved by the use of predominantly crystalline thermoplastic materials for the opaque wall members in accordance with this invention.

The above has been offered for illustrative purposes only, and is not intended to limit the invention of this application, which is as defined in the claims below.

That which is claimed is:

1. In a connector member for a fluid flow path which comprises a transparent housing enclosing opaque barrier membrane means blocking flow through said flow path, said barrier membrane means being adapted to be openable by exposure to radiant energy from the exterior through said transparent housing, the improvement comprising, in combination, said barrier membrane means being made of a significantly crystalline thermoplastic material.

2. The connector member of claim 1 in which said barrier membrane means has a crystalline melting temperature of at least essentially 200° C.

3. The connector member of claim 1 in which said predominantly crystalline thermoplastic material exhibits at least 35 percent crystallinity.

4. The connector member of claim 1 in which said barrier membrane has a thickness of 0.002 to 0.06 inch.

5. The connector member of claim 1 in which said barrier membrane means is poly(4-methyl-1-pentene).

6. The connector member of claim 1 in which said barrier membrane means is poly(butylene terephthalate).

7. The connector member of claim 1 in which said barrier membrane is a nylon polyamide.

8. In a connector member providing sealed connection, said connector member comprising a pair of hollow, transparent housings, the hollow interiors of each of said housings being sealed from the exterior, some of the wall of each housing comprising an opaque wall portion separating the hollow housing interior from the exterior, each opaque wall portion being sealed to the remainder of its transparent housing, said housings being positionable together with the opaque wall portions in facing contact with each other, and held in sealed, retentive relationship, whereby upon exposure of connected housings to radiant energy, the opaque wall portions in facing contact can fuse together and open an aperture therethrough, the improvement comprising said opaque wall portion being made of a significantly crystalline thermoplastic material.

9. The connector member of claim 7 in which said opaque wall portion has a crystalline melting temperature of at least 200° C.

10. The connector member of claim 8 in which said predominantly crystalline thermoplastic material exhibits at least 35 percent crystallinity.

11. The connector member of claim 8 in which said barrier membrane has a thickness of 0.002 to 0.06 inch.

12. The connector member of claim 8 in which said barrier membrane means is poly(4-methyl-1-pentene).

13. The connector member of claim 8 in which said barrier membrane means is poly(butylene terephthalate).

14. The connector member of claim 8 in which said barrier membrane is a nylon polyamide.

15. A connector element for providing sealed connection with a second connector element of similar design, said connector element comprising a hollow, transparent housing communicating with a conduit member, the hollow interior of said housing being sealable from the exterior, some of the wall of said housing comprising an opaque wall portion separating the hollow housing interior from the exterior and sealable by connection to said second connector element with said opaque wall portion in facing contact with a corresponding opaque wall portion of the second connector element, said facing opaque wall portions being adapted to be openable by exposure to radiant energy from the exterior through said transparent housing, and retention means carried by the connector element for retention to said second connector element, the improvement comprising, in combination:

said opaque wall portion being made of a significantly crystalline thermoplastic material.

16. The connector member of claim 11 in which said opaque wall portion has a crystalline melting temperature of at least 200° C.

17. The connector member of claim 15 in which said predominantly crystalline thermoplastic material exhibits at least 35 percent crystallinity.

18. The connector member of claim 15 in which said barrier membrane has a thickness of 0.002 to 0.06 inch.

19. The connector member of claim 15 in which said barrier membrane means is poly(4-methyl-1-pentene).

20. The connector member of claim 15 in which said barrier membrane means is poly(butylene terephthalate).

21. The connector member of claim 15 in which said barrier membrane is a nylon polyamide.

22. The connector element of claim 15 in which said opaque wall portion has a thickness of 0.002 to 0.06 inch.

* * * * *